(12) United States Patent
Gatlin et al.

(10) Patent No.: US 8,012,913 B2
(45) Date of Patent: Sep. 6, 2011

(54) DIAMINE TERMINATED PRIMARY AMINE-ALDEHYDE SULFUR CONVERTING COMPOSITIONS AND METHODS FOR MAKING AND USING SAME

(75) Inventors: Larry W. Gatlin, San Antonio, TX (US); Daniel R. Dostie, Floresville, TX (US); Timothy Eric Gatlin, Floresville, TX (US)

(73) Assignee: Clearwater International LLC, Houston, TX (US)

( * ) Notice: Subject to any disclaimer, the term of this patent is extended or adjusted under 35 U.S.C. 154(b) by 0 days.

(21) Appl. No.: 11/545,387

(22) Filed: Oct. 10, 2006

(65) Prior Publication Data

US 2007/0032693 A1    Feb. 8, 2007

Related U.S. Application Data

(62) Division of application No. 10/734,600, filed on Dec. 12, 2003, now Pat. No. 7,140,433.

(51) Int. Cl.
*C09K 8/52* (2006.01)

(52) U.S. Cl. ........ 507/239; 536/55.2; 564/471; 564/472

(58) Field of Classification Search .................. 507/239; 564/471, 472; 536/55.2
See application file for complete search history.

(56) References Cited

U.S. PATENT DOCUMENTS

| | | | |
|---|---|---|---|
| 2,390,153 A | 12/1945 | Kern | 260/72 |
| 3,722,589 A | 3/1973 | Smith et al. | 166/250.01 |
| 3,856,921 A | 12/1974 | Shrier et al. | 423/228 |
| 4,052,159 A | 10/1977 | Fuerst et al. | |
| 4,112,050 A | 9/1978 | Sartori et al. | 423/223 |
| 4,112,051 A | 9/1978 | Sartori et al. | 423/223 |
| 4,112,052 A | 9/1978 | Sartori et al. | 423/223 |
| 4,454,914 A | 6/1984 | Watanabe | 166/244.1 |
| 4,625,803 A | 12/1986 | Walhaug et al. | 166/310 |
| 4,748,011 A | 5/1988 | Baize | 423/228 |
| 4,945,992 A | 8/1990 | Sacco | 166/310 |
| 4,978,512 A | 12/1990 | Dillon | 423/226 |
| 5,074,991 A | 12/1991 | Weers | |
| 5,169,411 A | 12/1992 | Weers | |
| 5,347,004 A | 9/1994 | Rivers et al. | |
| 5,462,721 A * | 10/1995 | Pounds et al. | 423/226 |
| 5,488,103 A | 1/1996 | Gatlin | |
| 5,498,707 A * | 3/1996 | Gatlin | 536/55.2 |
| 5,674,377 A | 10/1997 | Sullivan, III et al. | |
| 5,688,478 A | 11/1997 | Pounds et al. | |
| 5,698,171 A * | 12/1997 | Trauffer et al. | 423/220 |

(Continued)

FOREIGN PATENT DOCUMENTS

CA    2125513    1/1995

(Continued)

OTHER PUBLICATIONS

English abstract of JP 10001561A.*

(Continued)

*Primary Examiner* — Alicia Toscano
(74) *Attorney, Agent, or Firm* — Robert W Strozier

(57) ABSTRACT

A new class of sulfur scavenging or converting compositions is disclosed comprising diamine terminated, amine-aldehyde adducts, where the adducts are substantially bimolecular amine-aldehyde adducts and the composition is substantially free of trimer and/or triazines. Methods for making and using the new class of sulfur scavenging or converting composition are also disclosed.

32 Claims, 7 Drawing Sheets

Total Facility Weekly BOE and Water Production Comparison

U.S. PATENT DOCUMENTS

| | | | |
|---|---|---|---|
| 5,744,024 | A | 4/1998 | Sullivan, III et al. |
| 5,980,845 | A | 11/1999 | Cherry |
| 6,054,417 | A | 4/2000 | Graham et al. |
| 6,267,938 | B1 | 7/2001 | Warrender et al. |
| 6,486,115 | B1 | 11/2002 | Weaver et al. ............ 510/417 |
| 2002/0049256 | A1 | 4/2002 | Bergeron, Jr. |
| 2005/0130847 | A1 | 6/2005 | Gatlin et al. |
| 2005/0137114 | A1 | 6/2005 | Gatlin et al. |
| 2005/0153846 | A1 | 7/2005 | Gatlin |
| 2005/0250666 | A1 | 11/2005 | Gatlin et al. |
| 2006/0116296 | A1 | 6/2006 | Kippie et al. |
| 2006/0194700 | A1 | 8/2006 | Gatlin et al. |

FOREIGN PATENT DOCUMENTS

| | | | |
|---|---|---|---|
| CA | 2007965 | | 2/1996 |
| GB | 775376 | | 10/1954 |
| JP | 10001461 | | 6/1988 |
| JP | 08151422 | | 11/1996 |
| JP | 10001461 | A * | 1/1998 |
| WO | WO 98/19774 | | 5/1998 |

OTHER PUBLICATIONS

English translation of DE4027300.*

Nayar et al, Kinetics and Mechanism of the Aniline-Formaldehyde Reaction in Acid Medium, Makromol. Chem. 179, 1783-1790 (1978).*

Sartori, F. and Savage, D.W., Sterically Hindered Amines for CO2 Removal from Gases, Ind. Eng. Chem. Fundam. 1983, 22, 239-249.

Fushslueger, U., Socher, G., Grether, H-J., Grasserbauer, M., Capillary Supercritical Fluid Chromatography/Mass Spectroscopy of Phenolic Mannich Bases with Dimethyl Ether Modified Ethane as Mobile Phase, Anal. Chem., 1999, 71, 2324-2333.

Kauffman, W.J., Observations on the Synthesis and Characterization of N,N',N"-Tris-(dimethylaminopropyly)hexahydro-s-triazine and isolable intermediates, XP009005168.

Delepine, M., Effect of Hydrogen Sulfide on Trimethyltrimethyl Triamine, Bull. Soc. Chim., 1896, 14, 889-891 (English Translation).

Delepine, M., Effect of Hydrogen Sulfide and Trimethyltrimethyl Triamine, Ann. Chim. Phys., 1896, 4, 114-133 (English Translation).

Paquin, A.M., Reaction of Primary Amines with Aliphatic Aldehydes, Chem. Ber., 1949, 82, 316-326 (English Translation).

Castillo, M., Avila, Y.S., Rodrigues, R.E., Viloria, A., H2S Liquid Scavengers, Their Corrosivity Properites and the Compatibility with Other Down Stream Processes, Corrosion 2000, paper 00491.

U.S. Appl. No. 10/734,600, filed Dec. 12, 2003, Gatlin et al.
U.S. Appl. No. 10/745,290, filed Dec. 23, 2003, Gatlin et al.
U.S. Appl. No. 10/754,487, filed Jan. 9, 2004, Gatlin.
U.S. Appl. No. 10/839,734, filed May 5, 2004, Gatlin et al.
U.S. Appl. No. 10/999,796, filed Nov. 29, 2004, Kippie et al.
U.S. Appl. No. 11/066,600, filed Feb. 25, 2005, Gatlin et al.
U.S. Appl. No. 11/328,432, filed Jan. 9, 2006, Wilson.
U.S. Appl. No. 11/293,859, filed Dec. 2, 2005, Kippie et al.
U.S. Appl. No. 11/298,547, filed Dec. 9, 2005, Gatlin et al.
U.S. Appl. No. 11/298,556, filed Dec. 9, 2005, Gatlin et al.
U.S. Appl. No. 11/339,303, filed Jan. 25, 2006, Lukos et al.
U.S. Appl. No. 11/554,834, filed Oct. 31, 2006, Venditto et al.

* cited by examiner

DIAMINE TERMINATED PRIMARY AMINE-ALDEHYDE SULFUR CONVERTING COMPOSITIONS AND METHODS FOR MAKING AND USING SAME

RELATED APPLICATIONS

This application is a divisional application of U.S. patent application Ser. No. 10/734,600, filed 12 Dec. 2003, now U.S. Pat. No. 7,140,433, issued Nov. 28, 2006.

BACKGROUND OF THE INVENTION

1. Field of the Invention

The present invention relates to a novel sulfur scavenger including a diamine terminated reaction product of a primary amine and an aldehyde under conditions to reduce or preclude triazine formation.

More particularly, the present invention relates a novel sulfur scavenger including a diamine terminated reaction product of a primary amine and an aldehyde, where at least one aldehyde is added to a solution of at least one alkylamine under conditions to reduce or preclude triazine formation to produce a sulfur scavenging composition that does not liberate aldehyde upon heating and where trace imines are chemically reduced by adding a reducing agent to the crude product prior to workup.

2. Description of the Related Art

Noxious sulfur species, such as hydrogen sulfide and thiols, are present in many industrial and waste management environments such as oil and gas production, refining, chemical processing and manufacturing, coal gasification, sewage treatment and other industrial and waste management process. Many compounds have been prepared and patented to reduce these noxious sulfur species converting them to higher molecular weight sulfur containing materials, many of which are water soluble or have a higher partition coefficient for water than hydrocarbon. Such scavengers are disclosed in U.S. Pat. Nos. 4,748,011; 4,978,512; 4,748,011; 4,978,512; 2,390,153; 3,856,921; 4,112,050; 4,112,051; and 4,112,052. Many of these compositions also have utility in converting other troublesome compounds such as carbon dioxide into more benign compounds. See "Sterically Hindered Amines for $CO_2$ Removal from Gases" in I & EC FUNDAMENTALS, Vol. 2, No. 22 (1983).

Although many sulfur scavengers have been prepared and used in these industrial and water management applications, there is still a need in the art for compositions to reduce, reduce to a desired level or eliminate noxious sulfur agents or other troublesome compounds that are thermally stable, contain little or no triazines or other compounds that are known to liberate aldehyde upon heating and have acceptable properties for use in capillary coiled tubing applications, application where small diameter tubing it inserted into a well to a given depth and chemical agents such as sulfur scavengers are injected into the well fluid through the tubing.

SUMMARY OF THE INVENTION

The present invention provides a sulfur scavenging composition including a diamine centered, oligomer or polymer of a bimolecular adduct of primary amines and aldehydes, where the composition preferably includes sufficient diamine so that the composition liberates little or no aldehyde upon heating and where the composition has a pH between about 9 and about 13, and preferably, between about 10 and about 12.5.

The present invention also provides a sulfur scavenging composition including oligomers and/or polymers formed by reacting a diamine and a primary amine-aldehyde reaction product, where the reaction product comprises substantially bimolecular adducts of primary amines aldehydes, where the composition preferably includes sufficient diamine so that the composition liberates little or no aldehyde upon heating and includes no or only trace amount of triazines.

The present invention also provides a sulfur scavenging composition including a compound of formula (I):

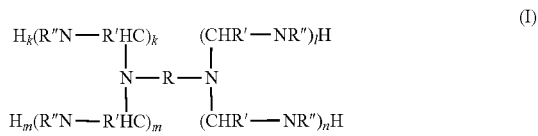

where R is an alkenyl group having between about 1 and about 20 carbon atoms, where one or more of the carbon atoms can be oxygen atoms in the form of ether, hydroxy and/or carboxy moieties and/or nitrogen atoms in the form of tertiary amine and/or amide moieties, R' and R" are the same or different carbon-containing groups having between about 1 and about 20 carbon atoms, where one or more of the carbon atoms can be oxygen atoms in the form of ether, hydroxy, and/or carboxy moieties and/or nitrogen atoms in the form of tertiary amine and/or amide moieties, where k, l, m and n are integers having a value between 0 and 2, provided that at least one have a have of 1 or 2, where the composition preferably liberates little or no aldehyde upon heating and includes no or only trace amounts of triazines.

The present invention provides a method for preparing sulfur scavenging compositions including the steps of adding at least one aldehyde to a solution including at least one primary amine under conditions to reduce or eliminate triazine formation and adding to the reaction at least one diamine. Preferably, the diamine is added in an amount sufficient to reduce or substantially eliminate liberation of aldehyde upon heating. The method can optionally include the step of hydrogenating any imine products to their corresponding saturated analog through the addition of a reducing agent such as sodium borohydride.

The present invention provides a method for converting noxious sulfur species to high molecular weight sulfur species including the steps of contacting a fluid or fluid stream including noxious sulfur species with an effective amount of a sulfur scavenging or converting composition including a compound of formula (I):

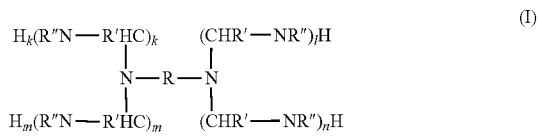

where R is an alkenyl group having between about 1 and about 20 carbon atoms, where one or more of the carbon atoms can be oxygen atoms in the form of ether, hydroxy and/or carboxy moieties and/or nitrogen atoms in the form of tertiary amine and/or amide moieties, R' and R" are the same or different carbon-containing groups having between about 1 and about 20 carbon atoms, where one or more of the carbon atoms can be oxygen atoms in the form of ether, hydroxy and/or carboxy moieties and/or nitrogen atoms in the form of tertiary amine and/or amide moieties, where k, l, m and n are integers having a value between 0 and 2, provided that at least one have a have of 1 or 2, where the composition preferably liberates substantially no aldehyde upon heating and includes no or only trace amounts of triazines, where the amount is sufficient to reduce, to reduce below a target level or to substantially eliminate the noxious sulfur species. By fluid the inventors means any combination of material including liquids, gases and/or solids that will flow at a particular operating temperature.

The present invention provides a method comprising the step of injecting into a fluid or fluid stream of a gas or oil production wellhead, a flowline, a separator, a tank, a line heater, a heater treater, or similar gas or oil handling and/or processing equipment an effective amount of a composition of this invention or a solution including a composition of this invention, where the amount is sufficient to reduce, reduce below a desired level or substantially eliminate noxious sulfur species in the fluid or fluid stream. The injecting step can be performed by chemical injection pumps, overpressure from a storage vessel with fluid or gas to facilitate entrance into sulfur containing fluid or fluid stream. The injecting step can also include passing the composition or solution containing the composition through an atomizer or nebulizer to finely distribute the composition or solution into the fluid or fluid stream. The injection step can be a single point or port injection format or preferably a multi-point or multi-port injection format, i.e., the composition or solution including the composition is introduced into the fluid or stream at multiple locations to improve sulfur conversion efficiency and effectiveness.

DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
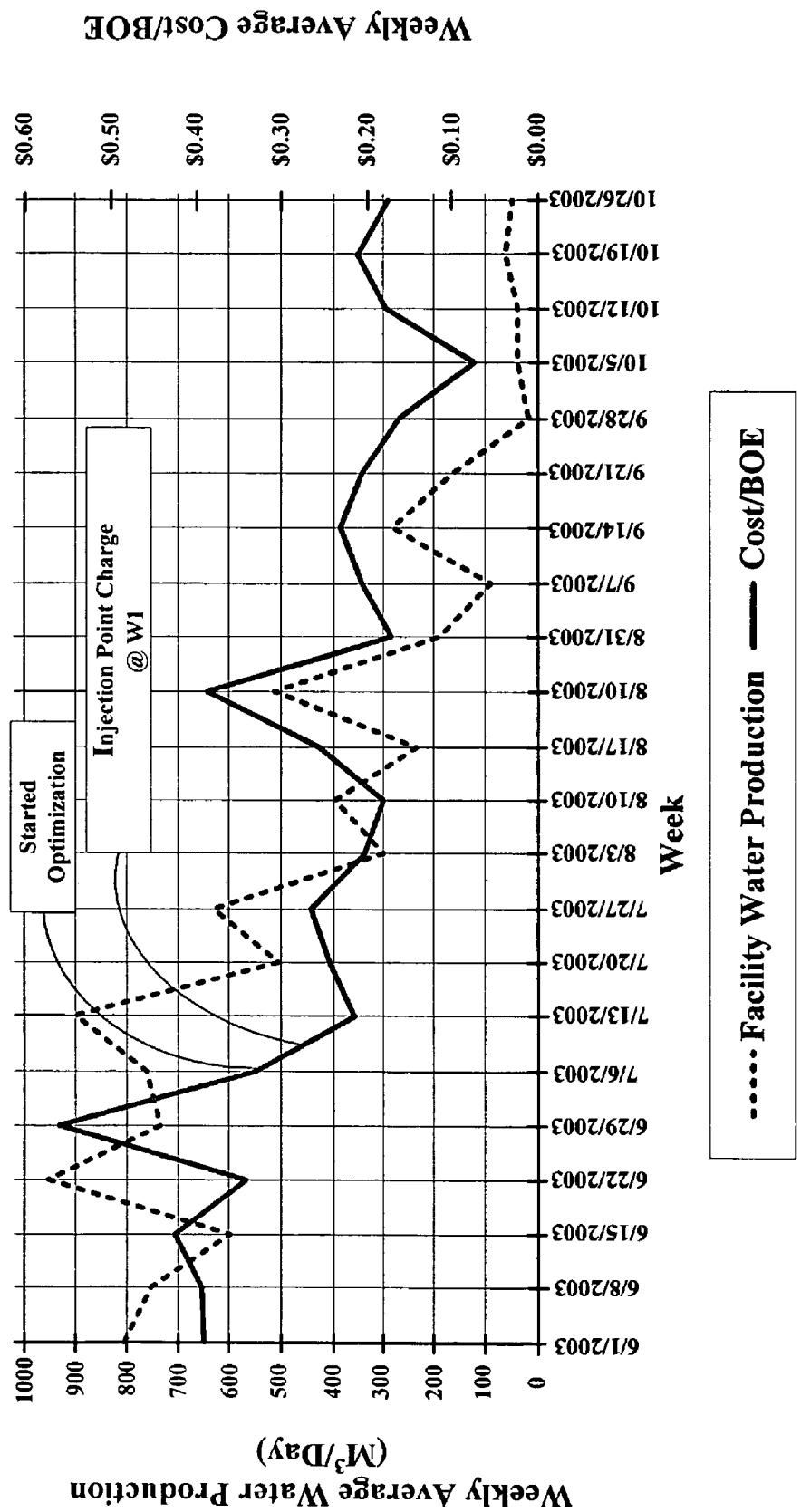
FIG. 1 depicts a plot of weekly average water production (M3/day) verses production week evidencing the effect of using a composition of this invention after optimization (adjusting amount bases on noxious sulfur content) and after multi-point injection of the composition into well fluids.

The inventors have found that a sulfur scavenging composition can be prepared by contacting at least one amine with at least one aldehyde under reaction conditions designed to reduce or eliminate triazine formation and terminating the reaction by the addition of at least one diamine, where the composition does not liberate aldehyde upon heating. The new sulfur scavenging compositions are ideally suited for converting noxious sulfur agents such as hydrogen sulfide, thiols or the like present in aqueous or non-aqueous fluid streams such as hydrocarbon-containing liquid, gas or mixed streams into water soluble compositions and for reducing below a given level or eliminating noxious sulfur compounds such as hydrogen sulfide ($H_2S$), thiol ($R^aSH$), or other odorous and/or corrosive sulfur-containing compounds.

The present invention broadly relates to sulfur scavenging compositions including diamine terminated bimolecular primary amine-aldehyde adduct, where the compositions do not liberate aldehyde upon heating and includes no or minimal amount of triazines.

The present invention broadly relates to sulfur scavenging compositions including a compound of formula (I):

$$[H_k(R''N-R'HC)][H_l(R''N-R'HC)]N-R-N[(CHR'-NR'')_mH][(CHR'-NR'')_nH] \quad (I)$$

where R is an alkenyl group having between about 1 and about 20 carbon atoms, where one or more of the carbon atoms can be oxygen atoms in the form of ether, hydroxy, and/or carboxy moieties and/or nitrogen atoms in the form of tertiary amine and/or amide moieties, R' and R" are the same or different carbon-containing groups having between about 1 and about 20 carbon atoms, where one or more of the carbon atoms can be oxygen atoms in the form of ether moieties and/or nitrogen atoms in the form of tertiary amine moieties or amide moieties, where k, l, m and n are integers having a value between 0 and 2, provided that at least one have a have of 1 or 2, where the composition does not liberate aldehyde upon heating and includes no or only trace amounts of triazines.

The present invention broadly relates to a method for preparing sulfur scavenging compositions including the steps of adding, under controlled conditions, at least one aldehyde or aldehyde donor to a solution of at least one primary amine under conditions to minimize trimer formation, a triazine precursor and to minimize aldol condensation and then terminating the reaction product with at least one diamine to produce diamine terminated amine-aldehyde oligomers and/or polymers which are thermally stable against aldehyde liberation, i.e., do not liberate aldehyde upon heating. Preferably, the diamine is present an amount sufficient to reduce, to reduce below a given level or substantially eliminate the liberation of aldehyde upon heating, where substantially eliminate means that the amount of liberated aldehyde is below the detection limit of a given aldehyde detector. Generally, the amount of diamine is between about 1 wt. % and about 25 wt. %, preferably, between about 2 wt. % and about 20 wt. %, particularly, between about 4 wt. % and about 20 wt. %. Of course, the exact amount will depend on the composition of the amine-aldehyde reaction product and the nature of the diamine or diamine mixture used to terminate the reaction product.

The present invention broadly relates to a method treating fluids containing noxious sulfur species including the steps of contacting the fluid with an effective amount of a sulfur scavenging composition of this invention singly, periodically or continuously to convert the noxious sulfur agents into a high molecular weight sulfur-containing adduct of the sulfur scavenging composition, preferably, a water soluble sulfur-containing adduct. The method can also include the steps of measuring a concentration of the noxious sulfur species in the fluid and added a concentration of the composition in excess of one to one, preferably two to one or more and then reducing the amount of composition until a desired level of noxious sulfur species is measured in the fluid. Of course, the latter step are associated with continuous application of the composition to the fluids.

The present invention provides a method comprising the step of filling or partially filling a bubble or percolating tower or vessel with a fluid and added to the fluid an effective amount of a composition of this invention or solution including a composition of this invention, where fluid is static or circulating countercurrent flow to gas percolating up from bottom of fluid column, and exiting through top of the tower or vessel(s) and where the effective amount is sufficient to reduce, reduce to a desired level or substantially eliminate noxious sulfur species in the fluid and/or gas during the percolation step.

The present invention provides a method comprising the step of contacting a fluid with an effective amount of a composition of this invention or solution including a composition of this invention, where the effective amount is sufficient to reduce, reduce to a desired level or substantially eliminate noxious sulfur species in the fluid. The fluid can be selected from the group consisting of natural gas, natural gas liquids, compressed liquids, crude oil, refined oils, refined oil products, oil/gas production associated water, other similar fluids and mixtures or combinations.

The present invention provides a method comprising the step of adding an effective amount of a composition of this invention or a solution including a composition of this invention to a fluid containing noxious sulfur species ($H_2S$/mercaptans or other sulfur compounds), where the fluid is a gas and/or liquid derived from a refinery, an industrial facility (chemical processing or the like) or a waste management facility such as sewage system off gas, bio-gas from composting, gases from land fills, etc. and where the effective amount is sufficient to reduce, reduce to a desired level or reduce the noxious sulfur species below a detectable level or to substantially eliminate the sulfur species.

The present invention provides a method comprising the step of adding an effective amount of a composition of this invention or a solution including a composition of this invention to a fluid containing noxious sulfur species ($H_2S$/mercaptans or other sulfur compounds), where the fluid is gases or liquids from coal bed methane recovery, or generation of gas from coal or syngas preparation and where the effective amount is sufficient to reduce, reduce to a desired level or reduce the noxious sulfur species below a detectable level or to substantially eliminate the sulfur species.

The present invention provides a method comprising the step of adding an effective amount of a composition of this invention or a solution including a composition of this invention to a fluid containing noxious sulfur species ($H_2S$/mercaptans or other sulfur compounds) to treat or sweeten the fluid, where the fluid comprises gas storage wells into wells as stored, during storage, and upon gas withdrawal and where the effective amount is sufficient to reduce, reduce to a desired level or reduce the noxious sulfur species below a detectable level or to substantially eliminate the sulfur species.

The present invention provides a method comprising the step of treating an refinery overhead streams including noxious sulfur species such as $H_2S$ with an effective amount of a composition of this invention or a solution including a composition of this invention, where the effective amount is sufficient to reduce, reduce to a desired level or reduce the noxious sulfur species below a detectable level or to substantially eliminate the sulfur species.

The present invention provides a method comprising the step of treating vapor areas of movable storage vessels such as barges or ships which contain vapors including noxious sulfur species such as $H_2S$ that accumulate during transit with an effective amount of a composition of this invention or a solution including a composition of this invention, where the effective amount is sufficient to reduce, reduce to a desired level or reduce the noxious sulfur species below a detectable level or to substantially eliminate the sulfur species.

The reaction products of this invention can be characterized by the following reaction scheme:

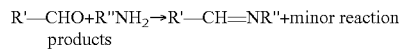
R'—CHO+R"NH$_2$→R'—CH=NR"+minor reaction products

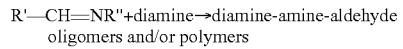
R'—CH=NR"+diamine→diamine-amine-aldehyde oligomers and/or polymers where R' and R" are as described above.

The compositions of this invention have increased efficiencies as compared to compositions including triazine analogs or imine analogs. The compositions of this invention are well suited for capillary coiled tubing down hold applications. The compositions of this invention are best used by adjusting the amount utilized until a concentration of the composition is about twice the amount of noxious sulfur species in the fluid and then reducing the amount added, while maintaining the conversion efficiency. The compositions of this invention also have a good tri-phasic partitioning property. Unlike many competitive product, the compositions of the present invention partition into the gas phase, hydrocarbon phase and aqueous phase with sufficient partitioning concentration to reduce, reduce to a given level or substantially eliminate (reduce below a given detectable limit) noxious sulfur species. Thus, unlike many competitive produce, the present compositions do not migrate substantially or totally to the aqueous phase, increasing the concentration of the composition at the hydrocarbon (organic phase)/gas interface. The tri-phasic behavior of the compositions of this invention make them ideally suited for multi-phase applications. Generally, the compositions of this invention are used as a solution of at least one compound of formula (I) in a solvent. The solution generally includes between about 0.5 ppm and about 500 ppm of the at least one compound of formula (I), preferably, between about 1 ppm and 100 ppm of the at least one compound of formula (I), particularly, between about 1 ppm and 50 ppm of the at least one compound of formula (I), more particularly, between about 1 ppm and 25 ppm of the at least one compound of formula (I), and especially between about 1 ppm and about 10 ppm relative to the solvent. Of course, greater and lesser amounts of the compounds of formula (I) can be used depending on the concentration of noxious sulfur species in the fluid to be treated as well as on other physical and chemical conditions such as temperature, volume, pressure, Alternatively, Typical application ratios for the compositions disclosed herein are from about 1 ppm to about 10 ppm, preferably, from about 2 ppm to about 4 ppm of sulfur scavenging composition per ppm of hydrogen sulfide in the fluid to be treated. This improved conversion allows more complete removal of hydrogen sulfide at a minimal cost, often without the need for a scrubber tower, which further reduces related equipment costs. The present compositions are active in two and three phase applications (two liquid phase and one gas phase).

Suitable primary amines for use in the preparation of the sulfur scavenging compositions of this invention include, without limitation, a primary amine of the formula R"NH$_2$ where R" is a linear or branched alkyl, aryl, alkaryl, or aralkyl group having between about 1 and about 20 carbon atoms and where one or more of the carbon atoms can be replaced by an oxygen atom or a nitrogen atom or nitrogen containing group provided that the oxygen atoms are in the form of ether, hydroxy and/or carboxy moieties and the nitrogen atoms are in the form of tertiary amine and/or amide moieties and one or more of the hydrogen atoms can be replaced by a fluorine atom or chlorine atom. Thus, the R" group can include one or more methylene oxide or ethylene oxide moieties in the carbon chain or one or more tertiary amine moieties in the carbon chain. Preferred R" groups include, without limitation, methyl, ethyl, propyl, isopropyl, butyl, sec-butyl, isobutyl, hexyls (linear or branched), hepyls, octyls, nonyls, decyls, phenyl, benzyl, methyl substituted phenyls, or mixtures or combinations thereof. Exemplary primary amines include, without limitation, methylamine, ethylamine, propylamine, isopropylamine, butylamine, sec-butylamine, iso-butylamine, hexylamines (all conformational types), heptylamines (all conformational types), octylamines (all conformational types), nonylamines (all conformational types), decylamines (all conformational types), etc. or mixtures or combinations thereof.

Suitable diamines and triamines for use in the preparation of the sulfur scavenging compositions of this invention include, without limitation, alkyl diamines, cycloalkyl diamines, alkacycloalkyl diamines, aralkyl diamines, aryl diamines, alkaryl diamines, amines heads or the like and analogs thereof and where one or more of the carbon atoms can be replaced with nitrogen atoms, oxygen atoms, or mixtures thereof where the oxygen atoms form carboxy, hydroxy and or ether moieties and the nitrogen atoms form tertiary amine and/or amide moieties and/or one or more hydrogen atoms can be replaced with fluorine atoms, chlorine atoms or mixture thereof and including between 2 and about 20 carbon atoms, preferably, about 3 to about 15 carbon atoms and particularly, about 4 to about 10 carbon atoms. Exemplary examples of alkyl diamines including, without limitation, 1,2-diaminoethane (1,2-ethylene diamine), 1,2-diaminopropane, 1,3-diaminopropane, 1,2-diaminobutane, 1,3-diaminobutane, 1,4-diaminobutane, 1,2-diaminopentane, 1,3-diaminopentane, 1,4-diaminopentane, 1,5-diaminopentane, and similar higher diaminoalkanes, aminomethylcyclopentylamine, 1,2-cyclopentanediamine, 1,6-hexanediamine, 1,2-diaminobenzene, lysine (or other diamine amino acids), 1,2-diaminobenzene, 1,4-diamine benzene, 1,2-diphenyl-1,2-ethane diamine, phenylene diamine, 2-hydroxypropylene diamine, hydantoin, N,N-Bis(dihydroxyethyl)ethylenediamine, hexahydrotriazine, aminoethylpiperazine (AEP) or the like, or mixtures or combinations thereof. Amine heads is commercially available from Monsanto Company and DuPont as a byproduct in the manufacture of hexamethylenediamine. Although the above listed aliphatic diamines are suitable for use in making the compositions of the invention, it should be understood that other diamines or triamines can be used as well. Examples of other aliphatic diamines and triamines that can be satisfactorily used in making the subject compositions include bis-hexamethylenetriamine.

As used herein, the term "amine heads" refers to an unrefined mixture of alkyl diamines that comprise from 4 to 6 carbon atoms. Examples of alkyl diamines typically found in amine heads include aminomethylcyclopentylamine; 1,2-cyclohexanediamine (1,2-diaminocyclohexane); 1,5-pentanediamine, 2-methyl; 1,6-hexanediamine; 1H-azepine, hexahydro; and 1,4-butanediamine. Amine heads is commercially available from Monsanto Company and DuPont as a byproduct in the manufacture of hexamethylenediamine.

Although amine heads is a convenient and useful source of aliphatic diamines suitable for use in making the compositions of the invention, it should be understood that other diamines or triamines not present in amine heads can likewise be used within the scope of the invention. Examples of other aliphatic diamines and triamines that can be satisfactorily used in making the subject compositions include 1,4-diaminocyclohexane and bis-hexamethylenetriamine.

Suitable diamines for use in this invention can also include, without limitation, diamines of the general formula

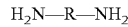

where R is linear or branched alkenyl groups having between about 1 and about 20 carbon atoms, cycloalkenyl groups having between about 1 and about 20 carbon atoms, alkylcycloalkenyl groups having between about 1 and about 20 carbon atoms, alka arenyl group having between about 1 and about 20 carbon atoms, ara alkenyl group having between about 1 and about 20 carbon atoms, or the like or mixtures or combinations thereof. Preferred alkenyl groups have between about 1 and about 10 carbon atoms. The R group can also include atoms other than carbon and hydrogen such as oxygen, nitrogen, fluorine and/or chlorine. Preferred groups including oxygen atoms in the form of hydroxy or ether moieties or nitrogen atoms in the form of tertiary amine or amide moieties.

Suitable aldehydes useful for making the subject compositions of this invention include, without limitation, aldehydes having the formula R'—CHO or aldehyde donors that generate such aldehydes, where R' is a hydrogen atom (H) or a linear or branched alkyl, aryl, alkaryl, or aralkyl group having between about 1 and about 20 carbon atoms and can include atoms other than carbon and hydrogen such as oxygen, nitrogen, fluorine and/or chlorine, provided that the oxygen atoms are in the form of ether or hydroxy moieties and nitrogen atoms in the form of tertiary amine and amide moieties. Thus, the R' group can include one or more methylene oxide or ethylene oxide moieties in the carbon chain or one or more tertiary amine or amide moieties in the carbon chain. Preferred R' groups include, without limitation, methyl, ethyl, propyl, isopropyl, butyl, sec-butyl, isobutyl, hexyls (linear or branched), hepyls, octyls, nonyls, decyls, phenyl, benzyl, methyl substituted phenyls, or mixtures or combinations thereof. Exemplary examples of aldehydes include, formaldehyde, paraformaldehyde, arylaldehydes, methoxyaldehydes, hydroxyaldehydes or aldols such as cinnaminaldehyde, glyceraldehydes, acetadol, paraldehyde (trimer of acetaldehyde), vanillin, veratraldehyde, alloxan, noneal, 1-formyl piperdine, salicylaldehyde, citronella or the like, or mixtures or combinations thereof. Preferred examples of aldehydes useful in this invention, include, without limitation, monoaldehydes having from 1 to 10 carbon atoms (one or more carbon atoms can be a non-carbon atoms including oxygen or nitrogen and can include fluorine and/or chlorine hydrogen substitutions) such as paraformaldehyde, formaldehyde, acetaldehyde, glycolaldehyde, glyceraldehyde, hydroxymethyl glyceraldehyde, glyoxal, and methyl formcel (a hemi-acetal, 55 percent formaldehyde solution in methanol and methoxy-methanol or water), aldols, or the like.

Aldehyde donors believed useful in making the compositions of the invention are preferably selected from the group consisting of hydantoin; hexamethylenetetramine; hexamethylolmelamine; 2-[(hydroxymethyl)amino]ethanol; 5,5-dimethylhydantoin; tris(hydroxymethyl)nitromethane; 2-nitro-2-methyl-1-propanol; 2-nitro-2-ethyl-1,3-propanediol; 2-nitro-1-butanol; and acetaldehyde ammonia.

Solvent systems comprising up to about 90 weight percent solvent in conjunction with the inventive compositions made by reacting primary amines with aldehydes under conditions to reduce or eliminate trimer and/or triazine formation followed by reaction termination with at least one diamine to form an oligomeric and/or polymeric diamine terminated amine-aldehyde compositions can be used as well. The presence of solvents in the reaction mixture during the reaction of amine and formaldehyde, for example, can reduce the formation of undesirable byproducts. Preferred solvents for use in the reaction system are methanol, methoxymethanol, diglymine, and mixtures thereof.

The solvents identified below are believed to be exemplary of those solvents that can enhance the efficiency of the subject compositions in various applications: water or methanol, or mixtures thereof; methoxymethanol or mixtures of methoxymethanol and methanol; dicyclopentadiene; formamide; solutions of oxo-alcohols and oxo-alcohol ethers; disulfide oil; glycols; excess polyfunctional amines such as diamines and triamines; terpenes; cyclohexene; d-limonene; m-pyrol; diglymine; neopentyl glycol; glycerin diglymine; and neopentyl glycol and glycerin or glycerol. A solvent such as Texaco Amine C-6 (comprising morpholine residues) or methyldiethanolamines or oligomers thereof can be used in place of diamines to suppress cross-linking, but do not remove free formaldehyde.

The use of catalysts in the compositions of the invention can be desirable for extending their useful conversion life, for improving the conversion of organic sulfides to a less noxious form, and for converting low molecular weight sulfide reaction products to higher oxidative forms. In most cases the use of up to about 5 weight percent catalyst in the reactive mixtures by which the subject compositions are produced is believed to be satisfactory for achieving the purposes described above.

Catalysts believed to be satisfactory for use in making the compositions of the invention include, for example, potassium or sodium borohydride in aqueous alkaline solution; catechol borane; ammonia; thiourea; aluminum chlorohydrate; aluminum hydroxide; urea; iron hydroxide; iron chelates; tris(hydroxymethyl)nitromethane; brass or copper; acetylacetonate chelate of titanium; sodium percarbonate; erythorbic acid; lactone; serine; sodium methylate; and the sodium salt of lauryl sarcosinate. Particularly preferred catalysts for use in the subject compositions are amine chelated brass, tris(hydroxymethyl)nitromethane, catechol borane, and sodium salt of lauryl sarcosinate.

Suitable reducing agents for use in the present invention include, without limitation, borohydrides such as sodium borohydride, lithium tri ethyl borohydride, or the like, aluminohydrides such as lithium aluminum hydride or the like. Although boro and alumino hydrides are preferred, any other reducing agent that does not interfere with the indicated transformations can also be used.

EXPERIMENTAL SECTION

General Synthetic Procedure

An primary alkyl amine is charged to a closed pressure reactor. A greater than one molar excess of an aldehyde is then added slowly to the amine with stirring, while maintaining the temperature below the boiling point of the amine, generally between about 20° F. and about 110° F. The temperature is maintained by cooling the reactor during the aldehyde addition process. The aldehyde addition can be incremental or continuous, but is performed at a rate that does not exceed the cooling capacity of the reactor. Preferably, the aldehyde is added as a formal, such as methyl formal or butyl formal and in the case of formaldehyde as a inhibited solution in methanol.

Once aldehyde addition has been completed, the reaction temperature is allowed to rise to between about 90° F. and about 105° F. and the reaction is stirred at temperature for about 1 hour to about 24 hours. If excess aldehyde is still present, then the reaction can be subjected to a digest step, where the temperature is raised to between about 140° F. and about 200° F.

After completion of the initial amine-aldehyde reaction, maintained at low temperature to reduce dimer and trimer (triazine) production, a diamine or mixture of diamines is added to the reaction product keeping the pH below about 12.5. The reaction is carried out between about 105° F. and about 121° F. for a period of time between about 4 and about 24 hours. The reaction can also be performed with the addition of a small amount of a formaldehyde or formaldehyde donor solution. If formaldehyde is used and not completely consumed, then an additional digest step can be performed.

Example 1

This example illustrates the preparation of a substantially monomeric amine-aldehyde starting material.

To an appropriately sized closed, pressurized reactor was charged 0.6074 moles of a 40% solution of methylamine in water. 0.6073 moles of a 37% solution of formaldehyde in water (may also contain 7 to 25 wt. % methanol) was added slowly with stirring to the amine solution, while maintaining the temperature of about 40° F. during the addition by cooling the reactor. The addition is sufficiently slow so that the reactor cooling capacity can maintain the reaction near 40° F. The reaction is then allowed to rise in temperature and stirred for 1 to 24 hours. The amine-aldehyde adduct comprises substantially a bimolecular amine-aldehyde adduct, where the term substantially means $\geq 80$ wt. % of a bimolecular amine-aldehyde adduct, preferably, $\geq 85$ wt. % of a bimolecular amine-aldehyde adduct, particularly, $\geq 90$ wt. % of a bimolecular amine-aldehyde adduct and more and particularly, $\geq 95\%$ of a bimolecular amine-aldehyde adduct.

Example 2

This example illustrates the preparation of a diamine-terminated sulfur scavenger/converter composition that, although is effective as a sulfur scavenger under optimized conditions, does not have the thermal stability regarding the formation of detectable quantities of aldehyde that more preferred compositions of this invention possess.

Based on an hundred weight percent formulation, 98 wt. % of an amine-aldehyde product of Example 1 was charged to an appropriately sized reactor. If the pH is above 10.5, then 1 wt. % of a 37% solution of formaldehyde in methanol was added, otherwise no formaldehyde was added. After formaldehyde addition, if required, 1 wt. % of amine heads was added to the reactor at a temperature between about 105° F. and about 121° F. for a period of time between about 4 and about 24 hours. After the reaction was complete, any imine was removed by hydrogenation with sodium borohydride or a similar reducing agent. The final pH of the reaction mixture is between about 9 and about 13, with a pH between about 10 and about 12.5 being preferred, depending on the amount of diamine added to the product of Example 1.

Example 3 the preparation of a diamine-terminated sulfur scavenger/converter composition that, although is effective as a sulfur scavenger under optimized conditions, does not have the thermal stability regarding the formation of detectable quantities of aldehyde that more preferred compositions of this invention possess.

To an appropriately sized reactor, 27828.08 lbs of a composition of Example 1 was charged and 250 lbs of formaldehyde followed by 283 lbs of amine heads. The reaction was stirred for 4 to 24 hours.

Example 4

This example illustrates the preparation of a preferred diamine-terminated sulfur scavenger/converter composition using the initial reaction product of Example 1 and N,N-bis(hydroxyethyl)ethylenediamine.

To an appropriately sized reactor, 393.69 gms of a composition of Example 1 was charged. The composition had an initial pH of 11.44. To this composition was added step-wise addition of the N,N-bis(hydroxyethyl)ethylenediamine. The composition was stirred for 1-4 hours and the pH measured after each incremental addition of diamine. Table I lists the total amount of diamine added, the wt % ratio and the pH after each addition.

TABLE I

Diamine Titration of Amine-Aldehyde Adduct

| Total Amount Added (grams) | pH | wt. % |
|---|---|---|
| 4.87 | 11.44 | 1.24 |
| 9.90 | 11.45 | 2.51 |
| 17.37 | 11.47 | 4.41 |
| 23.99 | 11.49 | 6.09 |
| 31.17 | 11.50 | 7.92 |
| 38.23 | 11.52 | 9.71 |
| 45.57 | 11.53 | 11.58 |
| 52.76 | 11.55 | 13.40 |
| 59.92 | 11.56 | 15.22 |
| 67.06 | 11.57 | 17.03 |
| 74.04 | 11.58 | 18.81 |
| 78.57 | 11.59 | 19.96 |

Example 5

This example illustrates the preparation of a preferred diamine-terminated sulfur scavenger/converter composition using the initial reaction product of Example 1 and Solutia Amine Heads (a mixture of DCH, HMD and TMD).

To an appropriately sized reactor, 500.28 gms of a composition of Example 1 was charged. The composition had an initial pH of 11.48. To this composition was added step-wise addition of the amine heads. The composition was stirred for 1-4 hours and the pH measured after each incremental addition of diamine heads. Table II lists the total amount of diamine heads added, the wt % ratio and the pH after each addition.

TABLE II

Diamine Titration of Amine-Aldehyde Adduct

| Total Amount Added (grams) | pH | wt. % |
|---|---|---|
| 2.38 | 11.50 | 0.48 |
| 4.49 | 11.53 | 0.90 |
| 6.72 | 11.55 | 1.34 |
| 8.92 | 11.59 | 1.78 |
| 11.05 | 11.61 | 2.21 |
| 13.28 | 11.63 | 2.65 |
| 15.62 | 11.65 | 3.12 |
| 17.92 | 11.68 | 3.58 |
| 20.34 | 11.71 | 4.07 |
| 22.83 | 11.72 | 4.56 |
| 25.23 | 11.74 | 5.04 |
| 27.43 | 11.76 | 5.48 |
| 29.67 | 11.77 | 5.93 |
| 31.79 | 11.78 | 6.35 |
| 33.78 | 11.79 | 6.75 |
| 35.86 | 11.81 | 7.17 |

Example 6

This example illustrates the preparation of a preferred diamine-terminated sulfur scavenger/converter composition using the initial reaction product of Example 3 and hexamethylenediamine.

To an appropriately sized reactor, 400.00 gms of a composition of Example 3 was charged. The composition had an initial pH of 10.46. To this composition was added step-wise addition of the N,N-bis(hydroxyethyl)ethylenediamine. The composition was stirred for 1-4 hours and the pH measured after each incremental addition of diamine. Table III lists the total amount of diamine added, the wt % ratio and the pH after each addition.

TABLE III

Diamine Titration of Amine-Aldehyde Adduct

| Total Amount Added (grams) | pH | wt. % |
|---|---|---|
| 4.42 | 11.25 | 1.11 |
| 6.26 | 11.37 | 1.57 |
| 8.17 | 11.46 | 2.04 |
| 10.29 | 11.55 | 2.57 |
| 12.52 | 11.61 | 3.13 |
| 14.85 | 11.67 | 3.71 |
| 16.99 | 11.72 | 4.25 |
| 19.21 | 11.76 | 4.80 |
| 21.58 | 11.80 | 5.48 |

Example 7

This example illustrates the aldehyde liberation in ppm of the compositions of Examples 3-6 upon heating in a microwave oven using an Environmental Sensor Company's Z300 Sensor using the instruction supplied by Environmental Sensor Company. The results are shown in Table IV.

TABLE IV

Aldehyde Liberation Test Upon Heating

| Composition | pH (neat) | Time Weighted Average Formaldehyde Liberation |
|---|---|---|
| Example 3 | 10.44 | 4.21 ppm for 60 seconds |
| Example 4 | 11.60 | 0.00 ppm for 30 seconds |
| Example 5 | 12.01 | 0.00 ppm for 80 seconds |
| Example 6 | 11.78 | 0.00 ppm for 80 seconds |

Clearly, the results of the aldehyde liberation test indicate that by adjusting the amount of diamine added to the intermediate amine-aldehyde reaction product of Example 1, sulfur scavengers that liberate substantially no detectable amount of formaldehyde can be prepared. These composition including a sufficient amount of diamine to suppress aldehyde liberation upon heating represent the preferred compositions of this invention from an environmental and health aspect. The compositions without the additional or optimized amount of diamine are acceptable sulfur scavengers for all applications, but do not have the preferred high temperature characteristics of the compositions of Examples 4-6. The compositions of Examples 4-6 are formed by reacting or contacting a reaction product of Example 1 with an effective amount of a diamine to form a diamine terminated-amine/aldehyde composition, where the effective amount of diamine is sufficient to reduce, reduce below a detectable level or substantially eliminate aldehyde liberation upon heating.

Noxious Sulfur Scavenging Data

Example 8

This example illustrates the effectiveness of the scavenger of Example 3 used in systems or well located in the Lady Fern field in Canada over a 21 week trial, where the amount and manner of introduction of the composition of Example 3 amount were optimized by adjusting the amount of composition to the amount of $H_2S$ present in the well fluids and by increasing the number of injection points for introducing the composition into the fluids. The test monitored water production, scavenger usage and other properties of the produced well fluids over the 21 week trial.

Referring now to FIG. 1, total facility weekly cost ratios (cost/BOE) and water production comparison data is shown over the 21 week trial using a composition of Example 3. The plot shows under initial conditions, facility water usage was up around 800 m³/day and cost/BOE was about $0.40. The amount of composition was then optimized which involved adding an excess of composition based on the amount of $H_2S$ in the fluids. It can be seen that optimization of composition concentration began to improve cost/BOE while water usage lagged. The optimization process continued where injection points were changed on well #1. It is clear that optimization of the amount of composition added and changes in the injection points brought water usage down to about 50 m³/day and cost was reduce to under $0.20.

Figure 2:
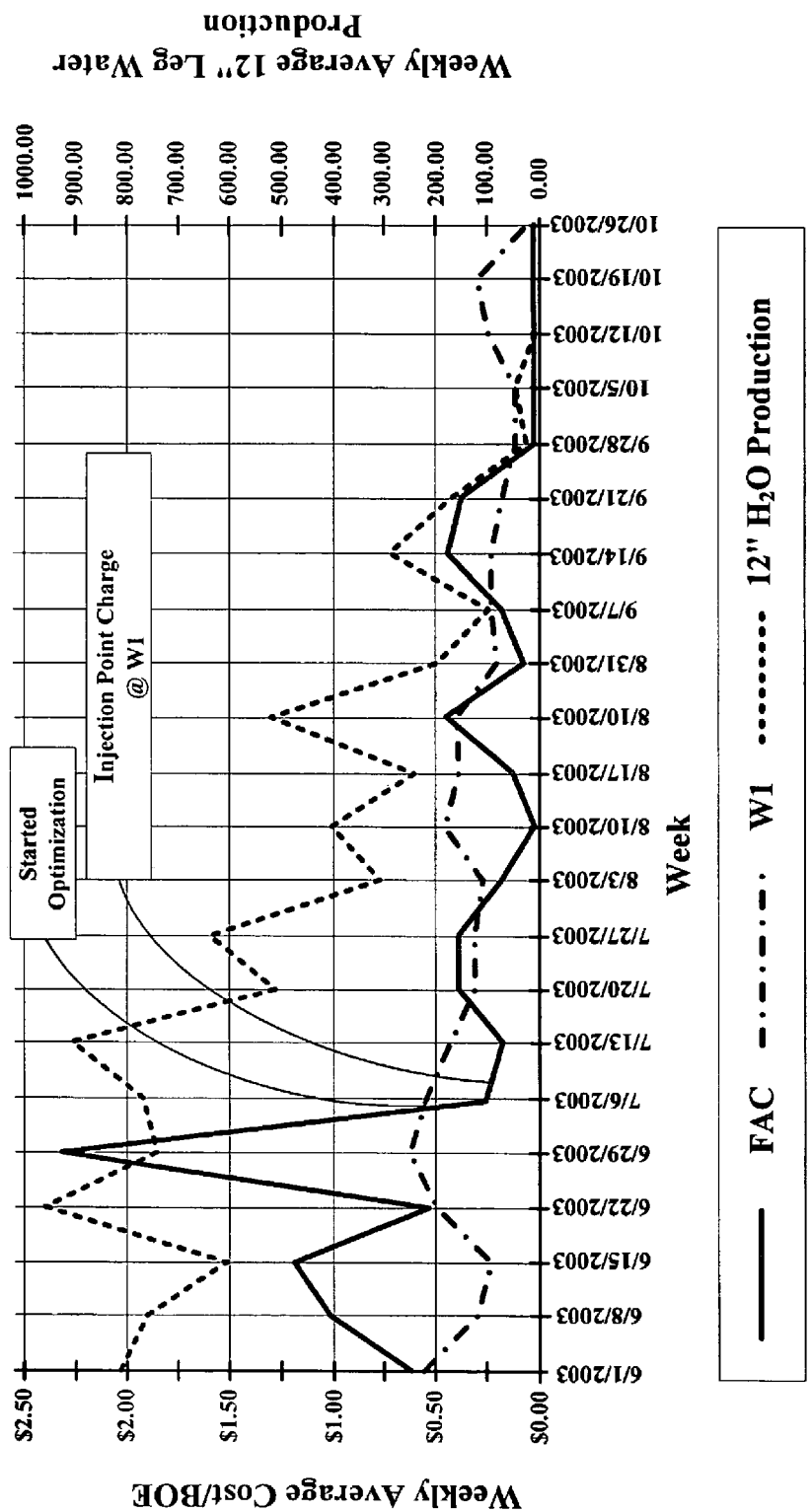
FIG. 2 depicts a plot of average weekly cost/BOE verses production week evidencing the effect of using a composition of this invention after optimization (adjusting amount bases on noxious sulfur content) and after multi-point injection of the composition into well fluids.

Referring now to FIG. 2, a plot of weekly average location specific cost/BOE and associated water production data is shown over the 21 week trial. Again, the data shows reductions in cost and water production for the production facility and well #1.

Figure 3:
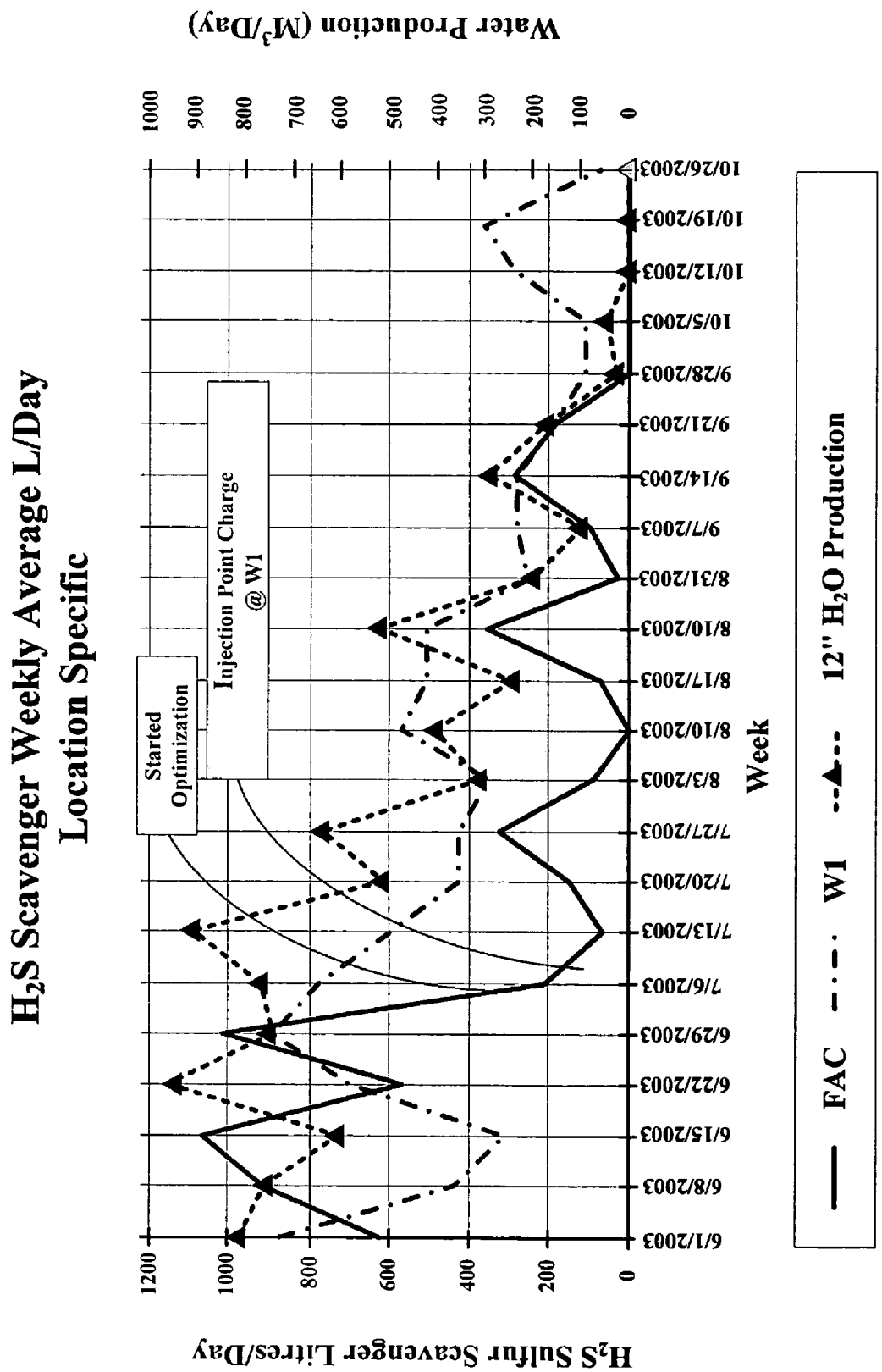
FIG. 3 depicts a plot of composition usage in liters/day verses production week evidencing the effect of using a composition of this invention after optimization (adjusting amount bases on noxious sulfur content) and after multi-point injection of the composition into well fluids.

Referring now to FIG. 3, a plot of composition weekly average usage (L/day) at specific locations. Again, the amounts of the composition of this invention and the 12" water production were significantly reduced after optimizing both the amount used and changing the injection points for the facility and well #1.

Figure 4:
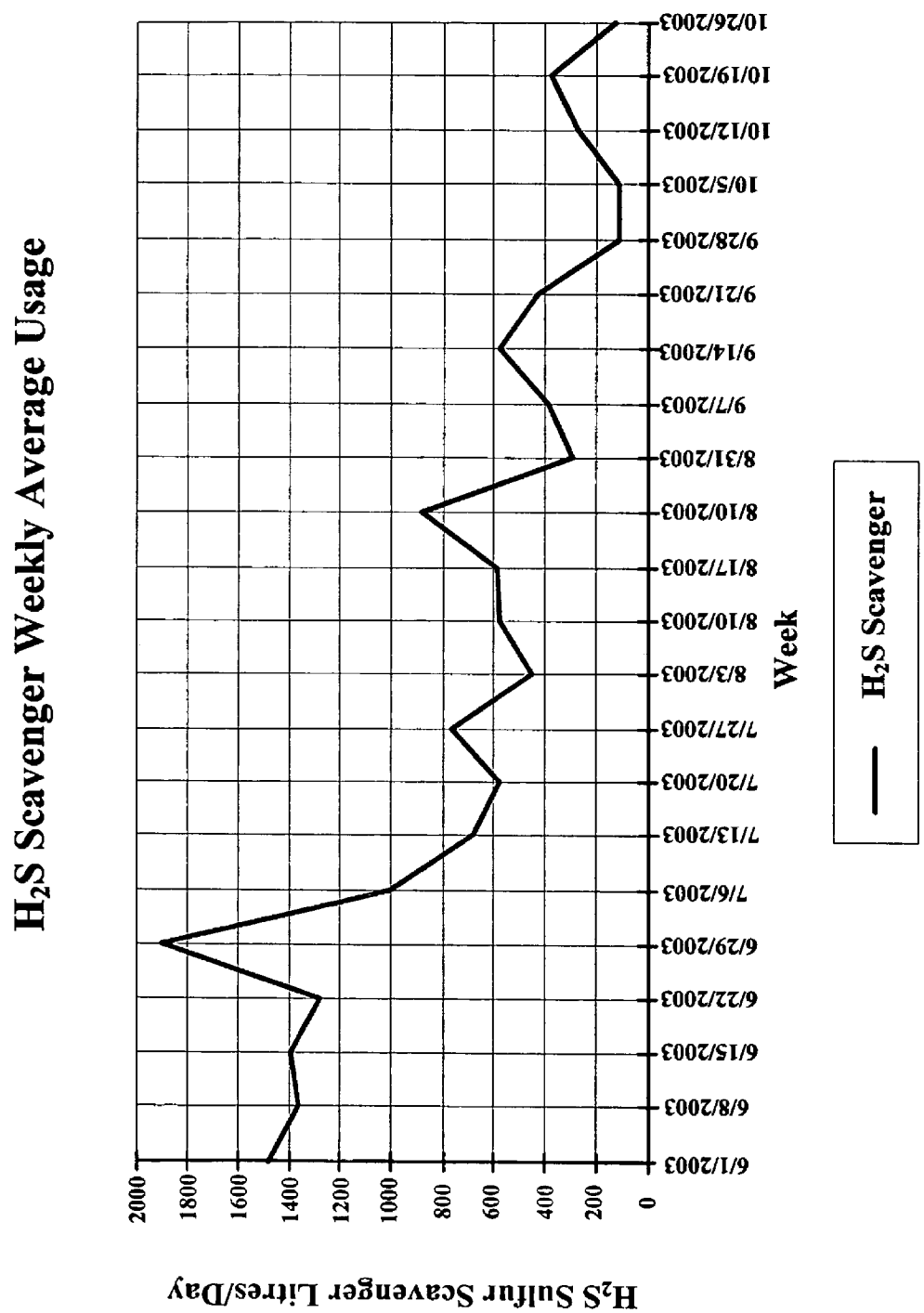
FIG. 4 depicts a plot of composition usage in liters/day verses production week evidencing the effect of using a composition of this invention after optimization (adjusting amount bases on noxious sulfur content) and after multi-point injection of the composition into well fluids.

Referring now to FIG. 4, a plot of the composition weekly average usage over the 21 week trial is shown. Again, the data shows a drop from over 1400 L/day at the start of the trial to a rate of about 100 L/day after optimization of both the amount used and the points of injection.

Figure 5:
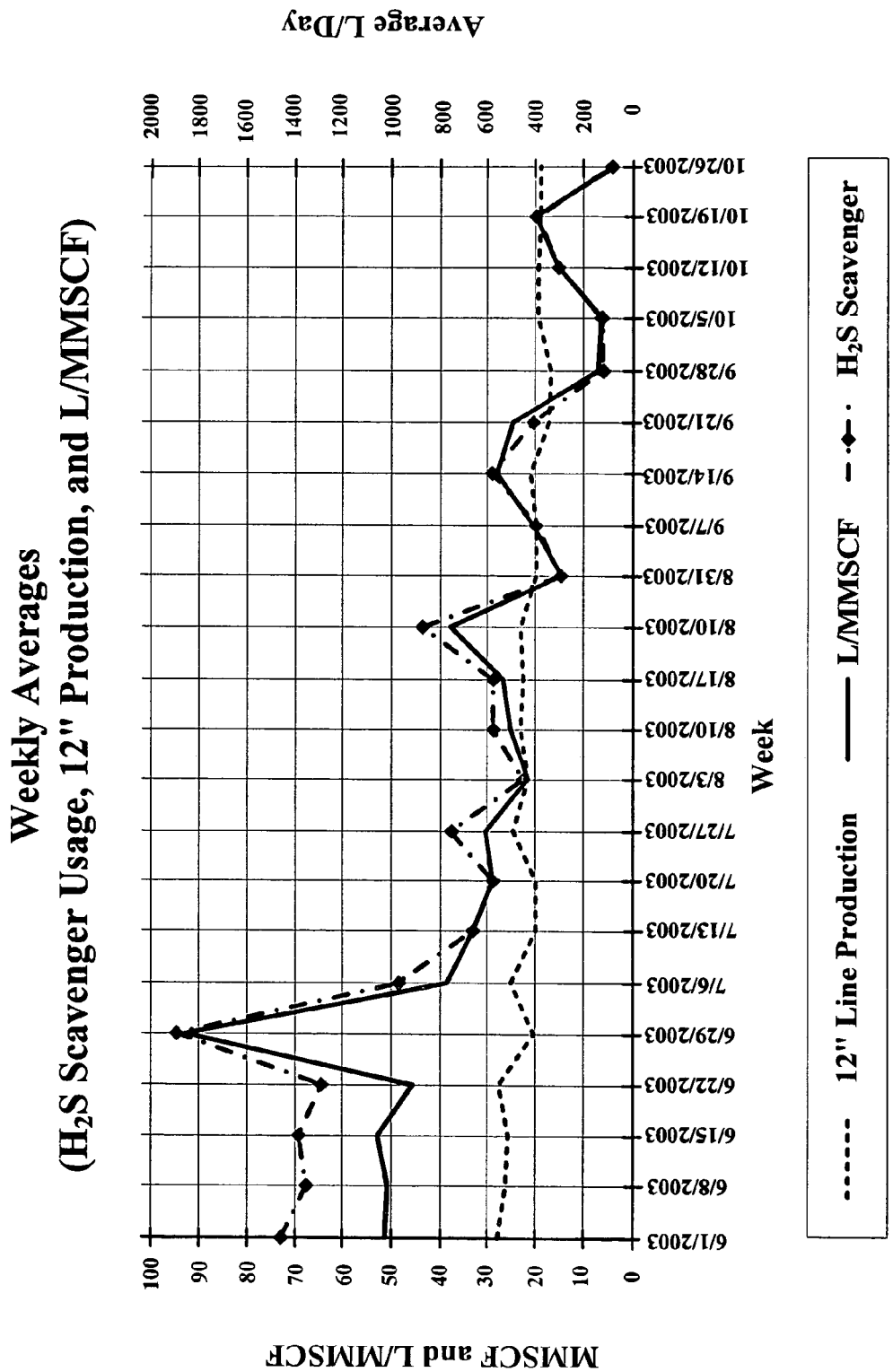
FIG. 5 depicts a plot of MMSCF and L/MMSCF verses production week evidencing the effect of using a composition of this invention after optimization (adjusting amount bases on noxious sulfur content) and after multi-point injection of the composition into well fluids.

Referring now to FIG. 5, a plot of weekly averages of composition usage, 12" line production and L/MMSCF is shown. Again, the data showed significant reductions in composition usage and in L/MMSCF ratio and a modest reduction in 12" line production.

Figure 6:
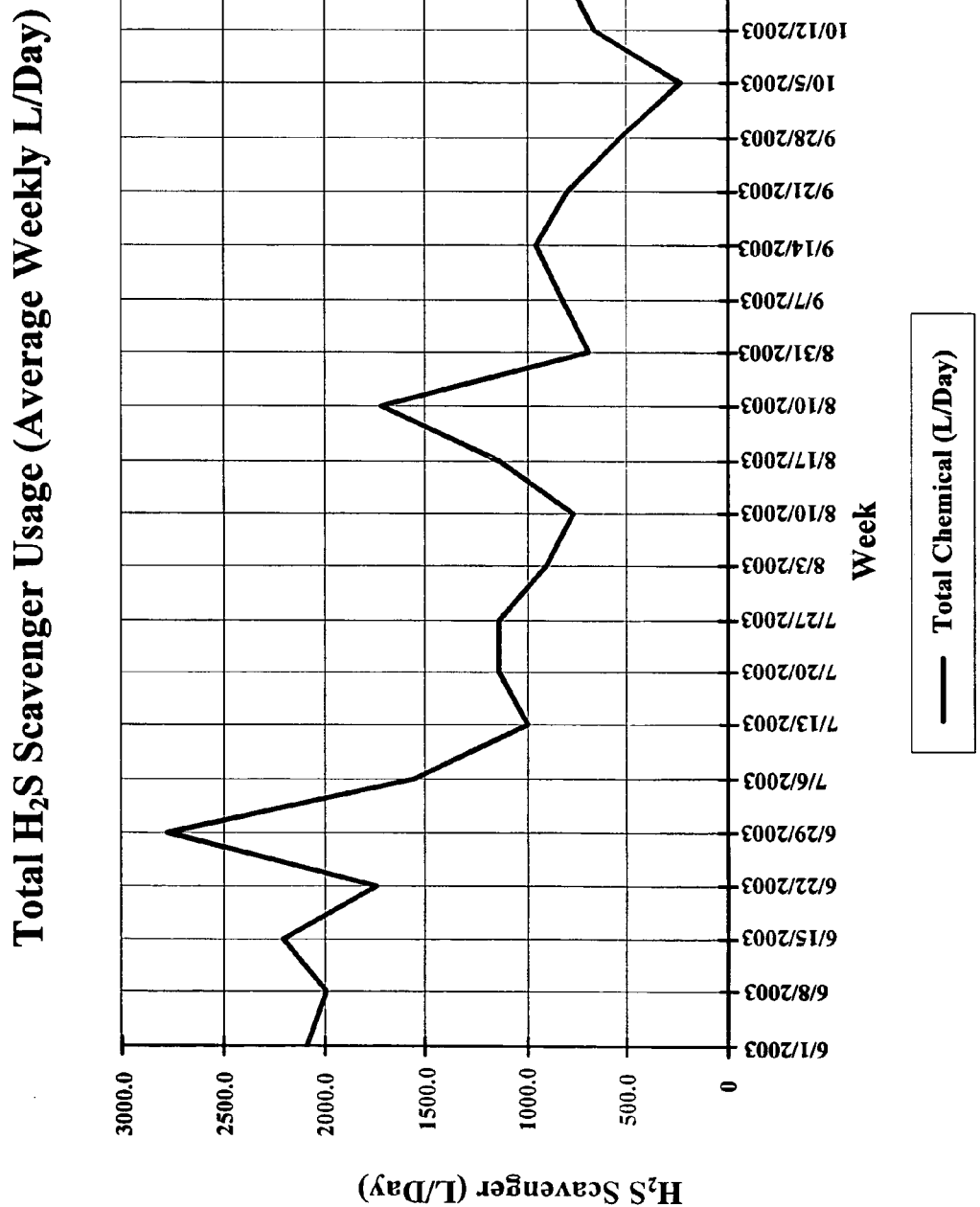
FIG. 6 depicts a plot of composition usage (L/Day) verses production week evidencing the effect of using a composition of this invention after optimization (adjusting a mount bases on noxious sulfur content) and after multi-point injection of the composition into well fluids.

Referring now to FIG. 6, a plot of total scavenger usage (average weekly L/day) is shown. Again, the initial usage was at about 2000 L/Day before optimization and was reduced to below about 750 L/day after optimization.

Figure 7:
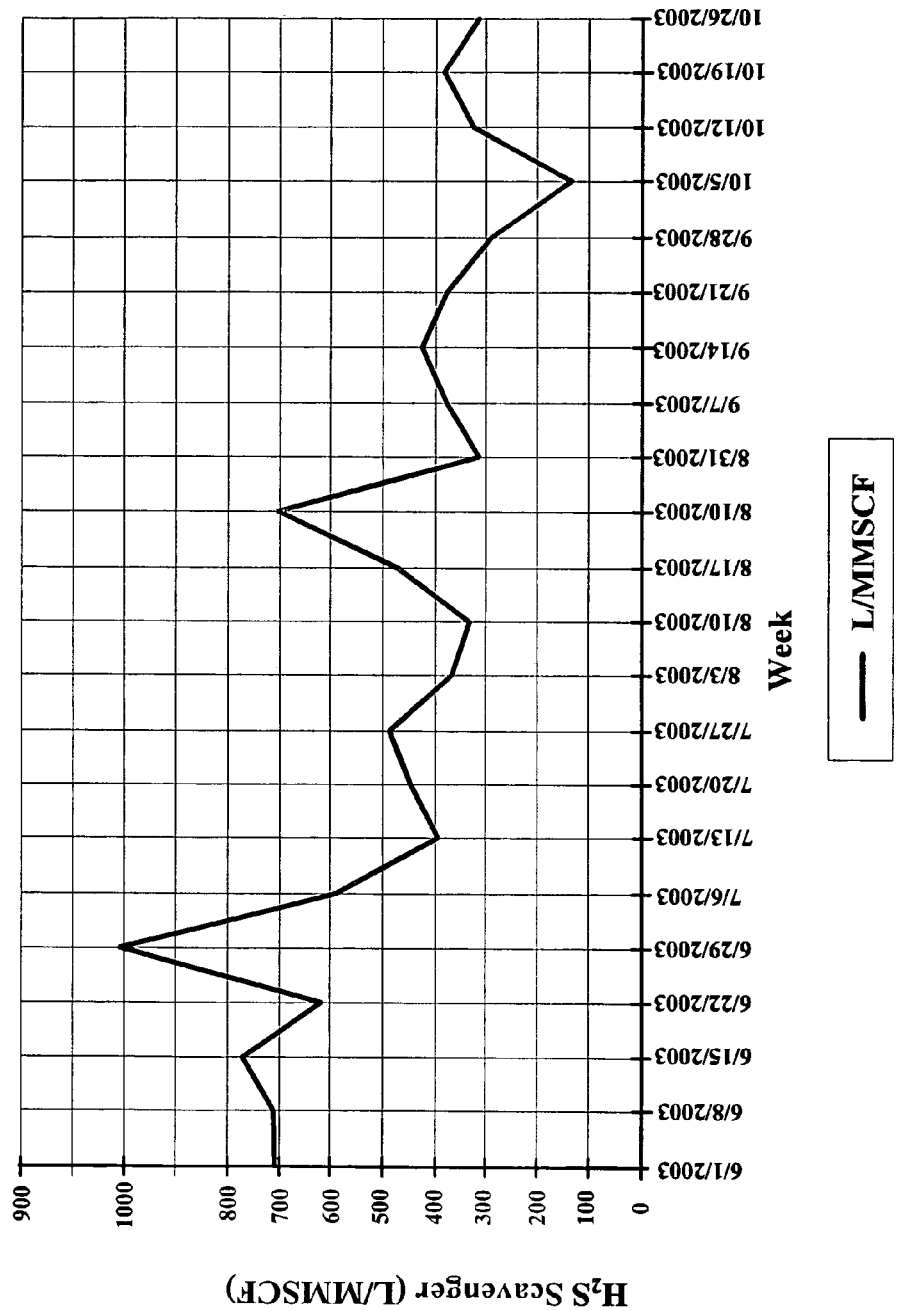
FIG. 7 depicts a plot of composition usage (L/Day) verses production week evidencing the effect of using a composition of this invention after optimization (adjusting amount bases on noxious sulfur content) and after multi-point injection of the composition into well fluids.

Referring now to FIG. 7, a plot of total facility average L/MMSCF ratio is shown. Again, the data showed a significant reduction in scavenger usage (L/MMSCF) over the 21 week trial from an initial value of about 35 L/MMSCF to about 15 L/MMSCF after amount and injection point optimization.

The testing data clearly evidences that the compositions of this invention a effective scavengers for application in cold climates and are well suited for partitioning in a tri-phasic environment providing cost effective noxious sulfur species removal.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A composition for converting noxious sulfur species to high molecular weight sulfur species comprising an effective amount of at least one compound having the general formula (I):

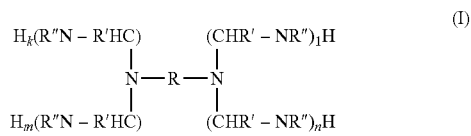

where:
the N—R—N moiety is derived from a diamine,
the R'CH moieties are derived from an aldehyde,
the R"N moieties are derived from a primary amine,
R is an alkenyl group, cycloalkenyl or arenyl group having between about 1 and about 20 carbon atoms, where one or more of the carbon atoms can be oxygen atoms in the form of carboxy, hydroxy and/or ether moieties and/or nitrogen atoms can be in the form of tertiary amine or amide moieties,
R' and R" are the same or different carbon-containing groups having between about 1 and about 20 carbon atoms, where one or more of the carbon atoms can be oxygen atoms in the form of carboxy, hydroxy and/or ether moieties or nitrogen atoms in the form of tertiary amine and/or nitrogen-containing groups in the form of amide moieties, k, l, m and n are integers, each having a value ranging from 1 to 2, and the effective amount is between about 0.5 ppm and about 500 ppm of the at least one compound of formula (I), and the composition liberates substantially no aldehyde upon heating, the composition includes no or only trace amount of triazines and the composition has a tri-phasic partitioning property so that the composition has a sufficient partitioning concentration in a tri-phase system comprising a gas phase, a hydrocarbon phase and an aqueous phase reducing noxious sulfur species, reducing to a given level noxious sulfur species or reducing below a given detectable limit noxious sulfur species simultaneously in all three phases of the tri-phase system.

2. The composition of claim 1, wherein R" is a methyl group, R' is H, and R is an cycloalkenyl group.

3. The composition of claim 1, wherein l, k, m and n are 1.

4. A method for preparing sulfur scavenging compositions including the steps of:

slowly adding an excess of at least one aldehyde to a solution including at least one primary amine, while maintaining a temperature of the solution at about 40° F. to form an amine-aldehyde composition comprising ≧80 wt. % of bimolecular amine-aldehyde adducts; and step-wise addition of at least one diamine to the product of the previous step to form a composition comprising at least one substituted diamine compound having the general formula (I):

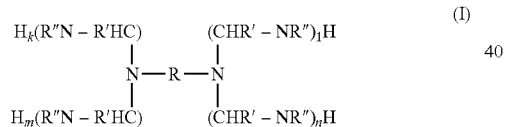

where:

N—R—N moiety is derived from a diamine,
R'CH moieties are derived from an aldehyde,
R"N moieties are derived from a primary amine,
R is an alkenyl group, cycloalkenyl or arenyl group having between about 1 and about 20 carbon atoms, where one or more of the carbon atoms can be oxygen atoms in the form of carboxy, hydroxy, and/or ether moieties and/or nitrogen atoms in the form of tertiary amine and/or amide moieties,
R' and R" are the same or different carbon-containing groups having between about 1 and about 20 carbon atoms, where one or more of the carbon atoms can be oxygen atoms in the form of carboxy, hydroxy and/or ether moieties or nitrogen atoms in the form of tertiary amine and/or nitrogen-containing groups in the form of amide moieties,
k, l, m and n are integers, each having a value ranging from 1 to 2,
the composition liberates substantially no aldehyde upon heating,
the composition includes no or only trace amount of triazines and the composition has a tri-phasic partitioning property so that the composition has a sufficient partitioning concentration in a tri-phase system comprising a gas phase, a hydrocarbon phase and an aqueous phase reducing noxious sulfur species, reducing to a given level noxious sulfur species or reducing below a given detectable limit noxious sulfur species simultaneously in all three phases of the tri-phase system.

5. The method of claim 4, further comprising the step of:
contacting the composition with a reducing agent to convert any imine by-products in the composition to their corresponding saturated analogs.

6. The method of claim 5, wherein the reducing agent is sodium borohydride.

7. The method of claim 4, wherein R" is a methyl group, R' is H, and R is an cycloalkenyl group.

8. The composition of claim 4, wherein l, k, m and n are 1.

9. A composition for converting noxious sulfur species to high molecular weight sulfur species comprising an effective amount of at least one compound having the general formula (I):

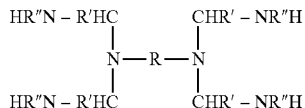

where:

N—R—N moiety is derived from a diamine,
R'CH moieties are derived from an aldehyde,
R"N moieties are derived from a primary amine,
R is an alkenyl group, cycloalkenyl or arenyl group having between about 1 and about 20 carbon atoms, where one or more of the carbon atoms can be oxygen atoms in the form of carboxy, hydroxy and/or ether moieties and/or nitrogen atoms can be in the form of tertiary amine or amide moieties,
R' and R" are the same or different carbon-containing groups having between about 1 and about 20 carbon atoms, where one or more of the carbon atoms can be oxygen atoms in the form of carboxy, hydroxy and/or ether moieties or nitrogen atoms in the form of tertiary amine and/or nitrogen-containing groups in the form of amide moieties,
the effective amount is between about 1 ppm and about 500 ppm of the at least one compound of formula (I), and
the composition liberates substantially no aldehyde upon heating,
the composition includes no or only trace amount of triazines and
the composition has a tri-phasic partitioning property so that the composition has a sufficient partitioning concentration is tri-phase system comprising a gas phase, a hydrocarbon phase and an aqueous phase reducing noxious sulfur species, reducing to a given level noxious sulfur species or reducing below a given detectable limit noxious sulfur species simultaneously in all three phases of the tri-phase system.

10. The composition of claim 9, wherein the primary amine is selected from the group consisting of amines of the general formula:

$R''NH_2$ where R" is a linear or branched alkyl, aryl, alkaryl, or aralkyl group having between about 1 and about 20 carbon atoms and where one or more of the carbon atoms can be oxygen atoms in the form of carboxy, hydroxy and/or ether moieties and/or nitrogen atoms can be in the form of tertiary amine or amide moieties, and one or more of the hydrogen atoms can be replaced by a fluorine atom or chlorine atom.

11. The composition of claim 9, wherein the aldehyde is selected from the group consisting of aldehydes of the general formula:

or aldehyde donors that generate such aldehydes, where R' is a hydrogen atom (H) or a linear or branched alkyl, aryl, alkaryl, or aralkyl group having between about 1 and about 20 carbon atoms and where one or more of the carbon atoms can be oxygen atoms in the form of carboxy, hydroxy and/or ether moieties and/or nitrogen atoms can be in the form of tertiary amine or amide moieties, and where one or more of the hydrogen atoms can be replaced by fluorine atoms and/or chlorine atoms.

12. The composition of claim 9, wherein the aldehyde is selected from the group consisting of the general formula:

or aldehyde donors that generate such aldehydes, where R' is selected from the group consisting of H, methyl, ethyl, propyl, isopropyl, butyl, sec-butyl, isobutyl, linear or branched hexyls, hepyls, octyls, nonyls, decyls, phenyl, benzyl, methyl substituted phenyls, and mixtures or combinations thereof.

13. The composition of claim 9, wherein the aldehyde is selected from the group consisting of formaldehyde, paraformaldehyde, arylaldehydes, methoxyaldehydes, hydroxyaldehydes or aldols, glyceraldehydes, vanillin, veratraldehyde, alloxan, noneal, 1-formyl piperidine, salicylaldehyde, citronella and mixtures or combinations thereof.

14. The composition of claim 9, wherein the aldehyde is selected from the group consisting of paraformaldehyde, paraldehyde, formaldehyde, acetaldehyde, glycolaldehyde, glyceraldehyde, hydroxymethyl glyceraldehyde, glyoxal, and methyl formcel (a hemi-acetal, 55 percent formaldehyde solution in methanol and methoxy-methanol or water), aldols, and mixtures or combinations thereof.

15. The composition of claim 9, wherein the diamine is selected from the group consisting of diamines of the general formula

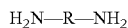

where R is linear or branched alkenyl groups having between about 1 and about 20 carbon atoms, cycloalkenyl groups having between about 1 and about 20 carbon atoms, alkylcycloalkenyl groups having between about 1 and about 20 carbon atoms, alka arenyl group having between about 1 and about 20 carbon atoms, ara alkenyl group having between about 1 and about 20 carbon atoms and mixtures or combinations thereof, where one or more of the carbon atoms can be oxygen atoms in the form of carboxy, hydroxy and/or ether moieties and/or nitrogen atoms can be in the form of tertiary amine or amide moieties, and where one or more of the hydrogen atoms can be replaced by fluorine atoms and/or chlorine atoms.

16. The composition of claim 9, wherein the primary amine is methyl amine, the aldehyde is formaldehyde and the diamine comprises alkyl diamines, where the alkyl group includes from 4 to 6 carbon atoms.

17. A sulfur scavenging composition comprising an effective amount of a substituted diamine including 4 substituents, two covalently bonded to each of the nitrogen atoms of the diamine, where ≧90% of the substituents are bimolecular amine-aldehyde adducts having the general formula —CHR'—NHR" or —CHR'—NR"—CHR'—NHR", where the adducts are prepared by a slow addition of an excess of an aldehyde to a primary amine, where the CHR' moieties are derived from the aldehyde, while maintaining a temperature of the solution at about 40° F., where the NR" moiety is or the NR" and the NHR" moieties are derived from the primary amine, where R' is a hydrogen atom (H) or a linear or branched alkyl, aryl, alkaryl, or aralkyl group having between about 1 and about 20 carbon atoms, where one or more of the carbon atoms can be oxygen atoms in the form of carboxy, hydroxy and/or ether moieties and/or nitrogen atoms can be in the form of tertiary amine or amide moieties, where one or more of the hydrogen atoms can be replaced by fluorine atoms and/or chlorine atoms, where R" is a linear or branched alkyl, aryl, alkaryl, or aralkyl group having between about 1 and about 20 carbon atoms, and where one or more of the carbon atoms can be oxygen atoms in the form of carboxy, hydroxy and/or ether moieties and/or nitrogen atoms can be in the form of tertiary amine or amide moieties, and one or more of the hydrogen atoms can be replaced by a fluorine atom or chlorine atom and where the composition liberates substantially no aldehyde upon heating, where the composition includes no or only trace amount of triazines, where the effective amount of the substituted diamine is between about 1 ppm and about 500 ppm, and where the composition has a tri-phasic partitioning property so that the composition has a sufficient partitioning concentration in a tri-phase system comprising a gas phase, a hydrocarbon phase and an aqueous phase reducing noxious sulfur species, reducing to a given level noxious sulfur species or reducing below a given detectable limit noxious sulfur species simultaneously in all three phases of the tri-phase system.

18. The composition of claim 17, wherein the primary amine is selected from the group consisting of amines of the general formula:

where R" is a linear or branched alkyl, aryl, alkaryl, or aralkyl group having between about 1 and about 20 carbon atoms and where one or more of the carbon atoms can be oxygen atoms in the form of carboxy, hydroxy and/or ether moieties and/or nitrogen atoms can be in the form of tertiary amine or amide moieties, and one or more of the hydrogen atoms can be replaced by a fluorine atom or chlorine atom.

19. The composition of claim 17, wherein the aldehyde is selected from the group consisting of aldehydes of the general formula:

or aldehyde donors that generate such aldehydes, where R' is a hydrogen atom (H) or a linear or branched alkyl, aryl, alkaryl, or aralkyl group having between about 1 and about 20 carbon atoms and where one or more of the carbon atoms can be oxygen atoms in the form of carboxy, hydroxy and/or ether moieties and/or nitrogen atoms can be in the form of tertiary amine or amide moieties, and where one or more of the hydrogen atoms can be replaced by fluorine atoms and/or chlorine atoms.

20. The composition of claim 17, wherein the aldehyde is selected from the group consisting of the general formula:

or aldehyde donors that generate such aldehydes, where R' is selected from the group consisting of H, methyl, ethyl, propyl, isopropyl, butyl, sec-butyl, isobutyl, linear or branched hexyls, hepyls, octyls, nonyls, decyls, phenyl, benzyl, methyl substituted phenyls, and mixtures or combinations thereof.

21. The composition of claim 17, wherein the aldehyde is selected from the group consisting of formaldehyde, paraformaldehyde, arylaldehydes, methoxyaldehydes, hydroxyaldehydes or aldols, glyceraldehydes, vanillin, veratraldehyde, alloxan, noneal, 1-formyl piperidine, salicylaldehyde, citronella and mixtures or combinations thereof.

22. The composition of claim 17, wherein the aldehyde is selected from the group consisting of paraformaldehyde, paraldehyde, formaldehyde, acetaldehyde, glycolaldehyde, glyceraldehyde, hydroxymethyl glyceraldehyde, glyoxal, and methyl formcel, aldols, and mixtures or combinations thereof.

23. The composition of claim 17, wherein the diamine is selected from the group consisting of diamines of the general formula

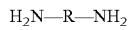

where R is linear or branched alkenyl groups having between about 1 and about 20 carbon atoms, cycloalkenyl groups having between about 1 and about 20 carbon atoms, alkylcycloalkenyl groups having between about 1 and about 20 carbon atoms, alka arenyl group having between about 1 and about 20 carbon atoms, ara alkenyl group having between about 1 and about 20 carbon atoms and mixtures or combinations thereof, where one or more of the carbon atoms can be oxygen atoms in the form of carboxy, hydroxy and/or ether moieties and/or nitrogen atoms can be in the form of tertiary amine or amide moieties, and where one or more of the hydrogen atoms can be replaced by fluorine atoms and/or chlorine atoms.

24. The composition of claim 17, wherein the primary amine is methyl amine, the aldehyde is formaldehyde and the diamine comprises alkyl diamines, where the alkyl group includes from 4 to 6 carbon atoms.

25. A sulfur scavenging composition comprising an effective amount of a substituted diamine including 4 substituents, two covalently bonded to each of the nitrogen atoms of the diamine, where ≧90% of the substituents are bimolecular amine-aldehyde adducts having the general formula —CHR'—NHR", where the adducts are prepared by a slow addition of an excess of an aldehyde to a primary amine, while maintaining a temperature of the solution at about 40° F., where the R'CH moiety is derived from an aldehyde, where the R"N moiety is derived from a primary amine, where a sufficient amount of diamine is used to substantially eliminate aldehyde liberation upon heating, where R' is a hydrogen atom (H) or a linear or branched alkyl, aryl, alkaryl, or aralkyl group having between about 1 and about 20 carbon atoms, where one or more of the carbon atoms can be oxygen atoms in the form of carboxy, hydroxy and/or ether moieties and/or nitrogen atoms can be in the form of tertiary amine or amide moieties, where one or more of the hydrogen atoms can be replaced by fluorine atoms and/or chlorine atoms, where R" is a linear or branched alkyl, aryl, alkaryl, or aralkyl group having between about 1 and about 20 carbon atoms and where one or more of the carbon atoms can be oxygen atoms in the form of carboxy, hydroxy and/or ether moieties and/or nitrogen atoms can be in the form of tertiary amine or amide moieties, and one or more of the hydrogen atoms can be replaced by a fluorine atom or chlorine atom, where the effective amount of the substituted diamine is between about 1 ppm, where the composition includes no or only trace amount of triazines and where the composition has a triphasic partitioning property so that the composition has a sufficient partitioning concentration is tri-phase system comprising a gas phase, a hydrocarbon phase and an aqueous phase reducing noxious sulfur species, reducing to a given level noxious sulfur species or reducing below a given detectable limit noxious sulfur species simultaneously in all three phases of the tri-phase system.

26. The composition of claim 25, wherein the primary amine is selected from the group consisting of amines of the general formula:

where R" is a linear or branched alkyl, aryl, alkaryl, or aralkyl group having between about 1 and about 20 carbon atoms and where one or more of the carbon atoms can be oxygen atoms in the form of carboxy, hydroxy and/or ether moieties and/or nitrogen atoms can be in the form of tertiary amine or amide moieties, and one or more of the hydrogen atoms can be replaced by a fluorine atom or chlorine atom.

27. The composition of claim 25, wherein the aldehyde is selected from the group consisting of aldehydes of the general formula:

or aldehyde donors that generate such aldehydes, where R' is a hydrogen atom (H) or a linear or branched alkyl, aryl, alkaryl, or aralkyl group having between about 1 and about 20 carbon atoms and where one or more of the carbon atoms can be oxygen atoms in the form of carboxy, hydroxy and/or ether moieties and/or nitrogen atoms can be in the form of tertiary amine or amide moieties, and where one or more of the hydrogen atoms can be replaced by fluorine atoms and/or chlorine atoms.

28. The composition of claim 25, wherein the aldehyde is selected from the group consisting of the general formula:

or aldehyde donors that generate such aldehydes, where R' is selected from the group consisting of H, methyl, ethyl, propyl, isopropyl, butyl, sec-butyl, isobutyl, linear or branched hexyls, hepyls, octyls, nonyls, decyls, phenyl, benzyl, methyl substituted phenyls, and mixtures or combinations thereof.

29. The composition of claim 25, wherein the aldehyde is selected from the group consisting of formaldehyde, paraformaldehyde, arylaldehydes, methoxyaldehydes, hydroxyaldehydes or aldols, glyceraldehydes, vanillin, veratraldehyde, alloxan, noneal, 1-formyl piperidine, salicylaldehyde, citronella and mixtures or combinations thereof.

30. The composition of claim 25, wherein the aldehyde is selected from the group consisting of paraformaldehyde, paraldehyde, formaldehyde, acetaldehyde, glycolaldehyde, glyceraldehyde, hydroxymethyl glyceraldehyde, glyoxal, and methyl formcel, aldols, and mixtures or combinations thereof.

31. The composition of claim 25, wherein the diamine is selected from the group consisting of diamines of the general formula

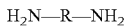

where R is linear or branched alkenyl groups having between about 1 and about 20 carbon atoms, cycloalkenyl groups having between about 1 and about 20 carbon atoms, alkylcycloalkenyl groups having between about 1 and about 20 carbon atoms, alka arenyl group having between about 1 and about 20 carbon atoms, ara alkenyl group having between about 1 and about 20 carbon atoms and mixtures or combinations thereof, where one or more of the carbon atoms can be oxygen atoms in the form of carboxy, hydroxy and/or ether moieties and/or nitrogen atoms can be in the form of tertiary amine or amide moieties, and where one or more of the hydrogen atoms can be replaced by fluorine atoms and/or chlorine atoms.

32. The composition of claim 25, wherein the primary amine is methyl amine, the aldehyde is formaldehyde and the diamine comprises alkyl diamines, where the alkyl group includes from 4 to 6 carbon atoms.

* * * * *